(12) United States Patent
Fay

(10) Patent No.: US 6,231,617 B1
(45) Date of Patent: May 15, 2001

(54) PROSTHETIC LINER HAVING LONGITUDINAL INELASTICITY

(76) Inventor: John N. Fay, 1120 Boca Ciega Isle, St. Petersburg, FL (US) 33706

( * ) Notice: Subject to any disclaimer, the term of this patent is extended or adjusted under 35 U.S.C. 154(b) by 0 days.

(21) Appl. No.: 09/352,107

(22) Filed: Jul. 14, 1999

(51) Int. Cl.$^7$ ...................................................... A61F 2/78
(52) U.S. Cl. ............................................................ 623/36
(58) Field of Search ............................................. 623/32–37

(56) References Cited

U.S. PATENT DOCUMENTS 5,728,167 * 3/1998 Lohmann ................................ 623/36

* cited by examiner

Primary Examiner—David H. Willse
(74) Attorney, Agent, or Firm—Ronald E. Smith; Smith & Hopen, P.A.

(57) ABSTRACT

A cushioned prosthetic liner includes a distal attachment plate to which is secured a number of longitudinally extending elongate arms that are substantially non-stretchable in a longitudinal direction. The arms allow radial expansion and contraction of the liner but substantially inhibit axial stretching and therefore inhibit milking of a residuum. The arms may be embedded within the liner or secured to a surface of the liner. The structure spreads the negative pressure generated during the swing phase of a gait over substantially all of the inner surface area of the liner to further inhibit the milking effect. The elongate arms are preferably formed of silk, fiberglass cloth, or other substantially non-stretchable material. They may also be provided in the form of a strip of epoxy applied to a surface of a conventional prosthetic liner or in the form of seams sewed into the liner. Additional embodiments include prosthetic liners having no distal attachment plate. In those additional embodiments, the non-stretchable elongate arms are embedded into or secured to the surface of the prosthetic liner.

17 Claims, 5 Drawing Sheets

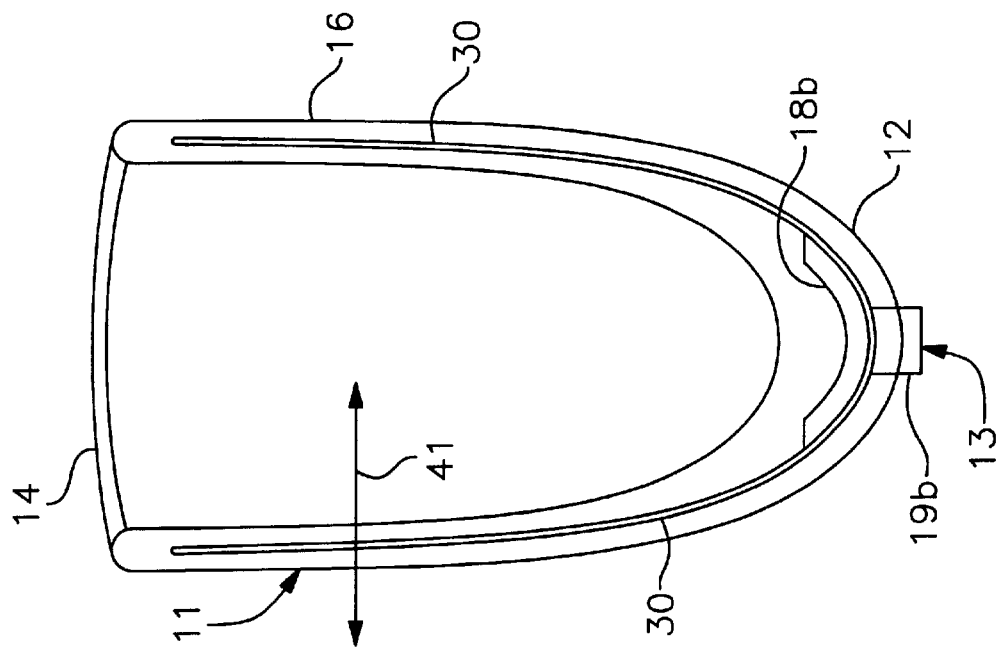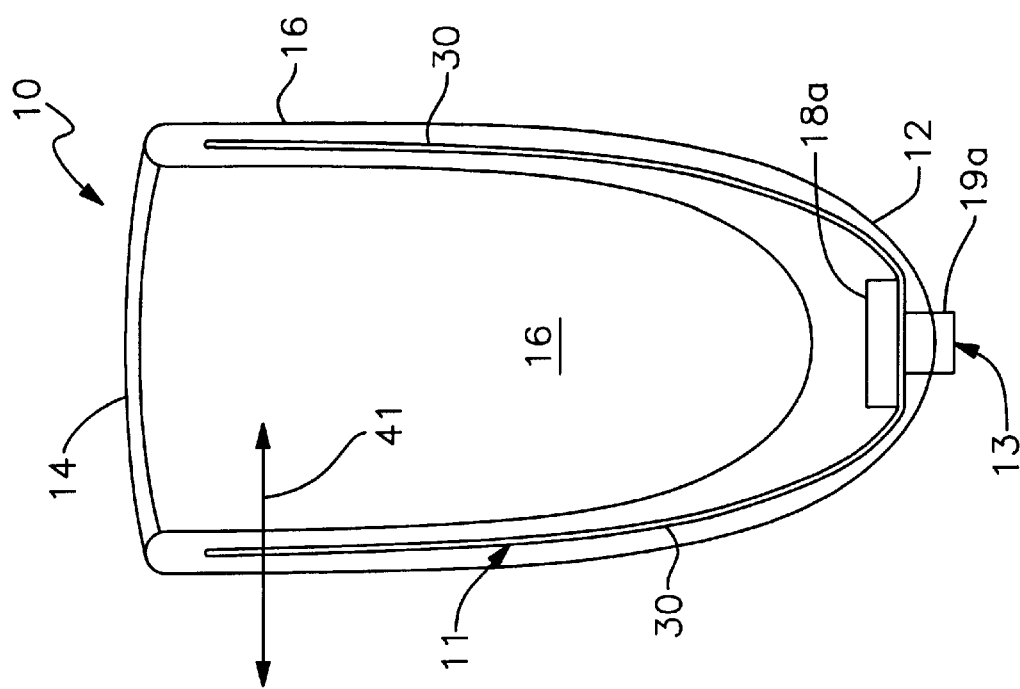

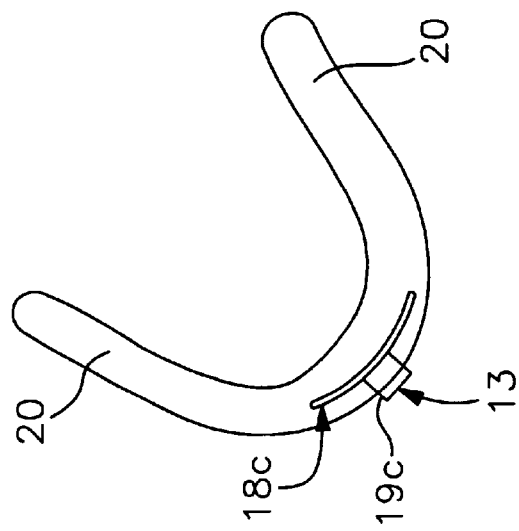
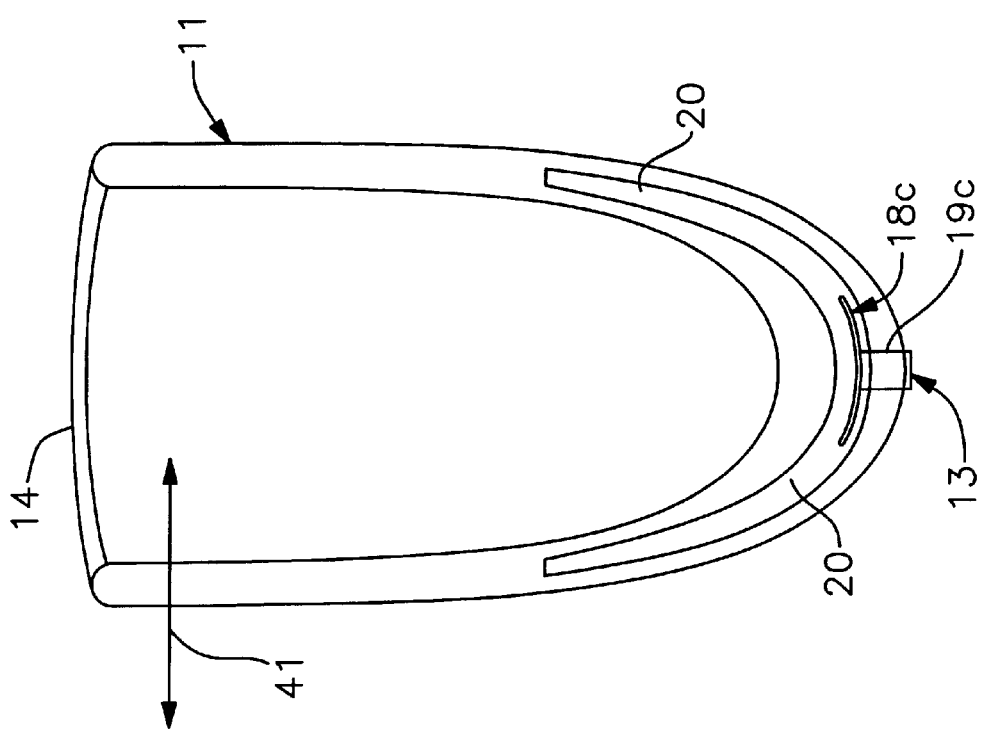

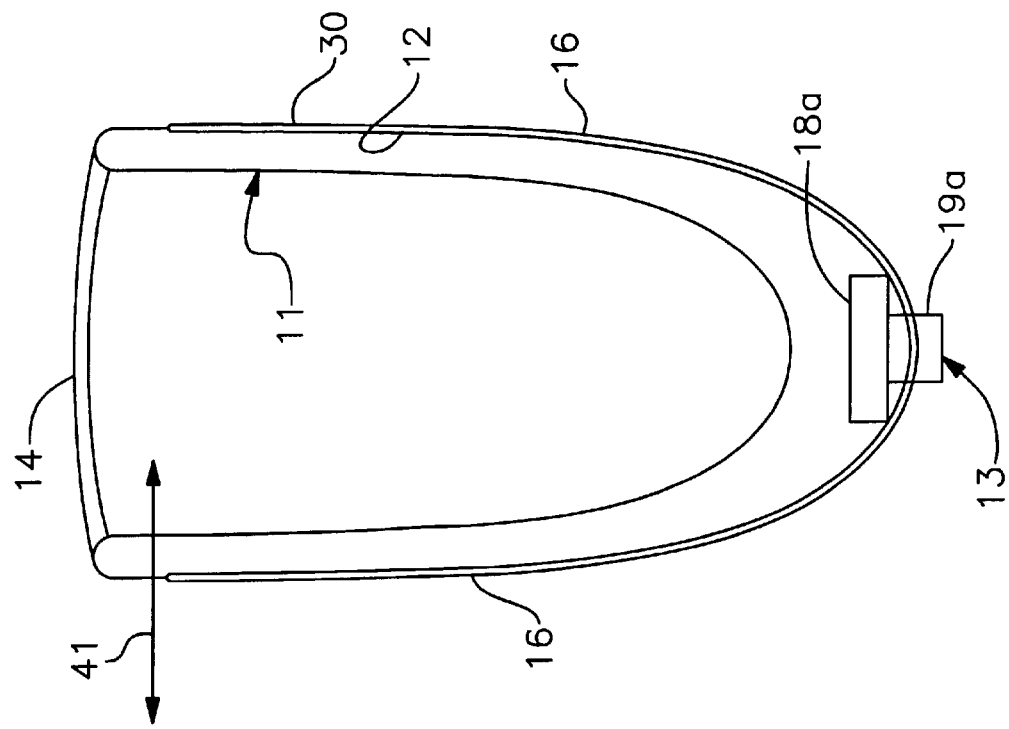
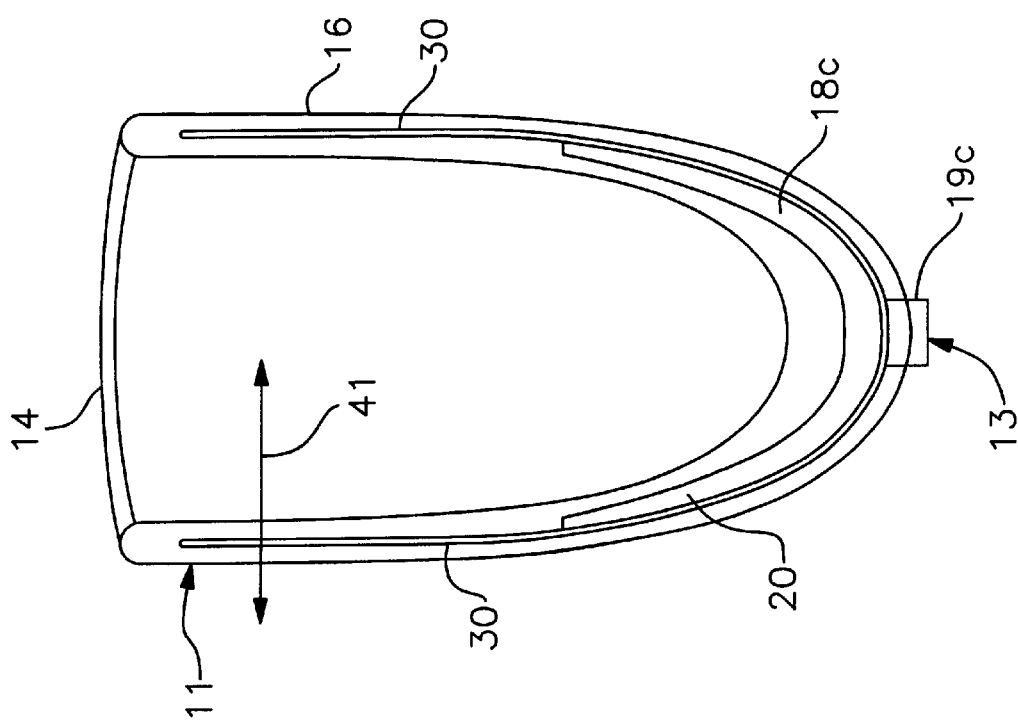

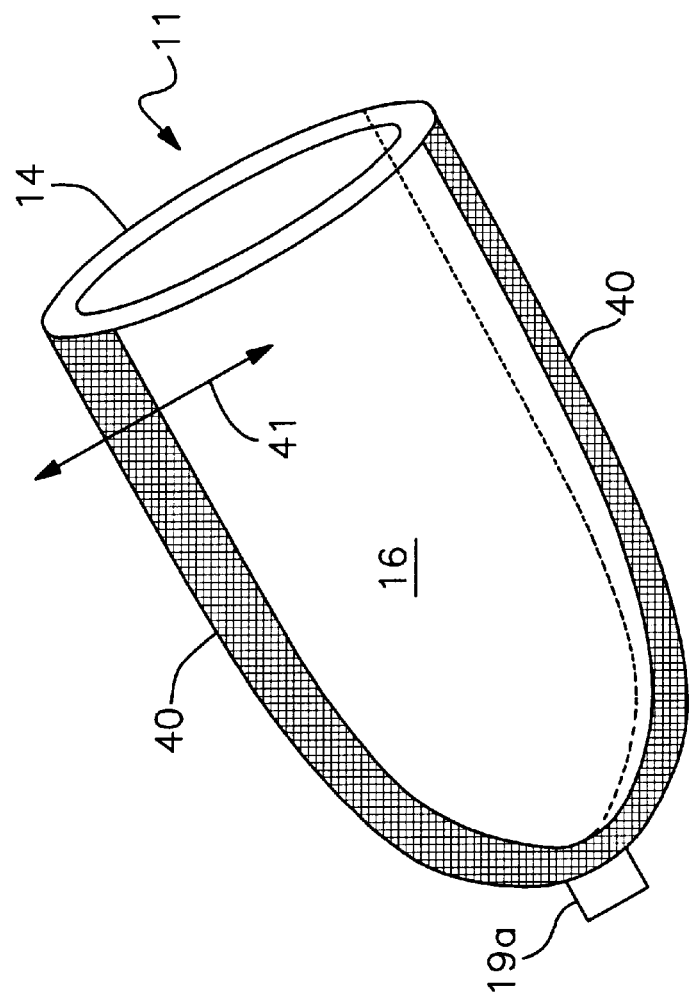
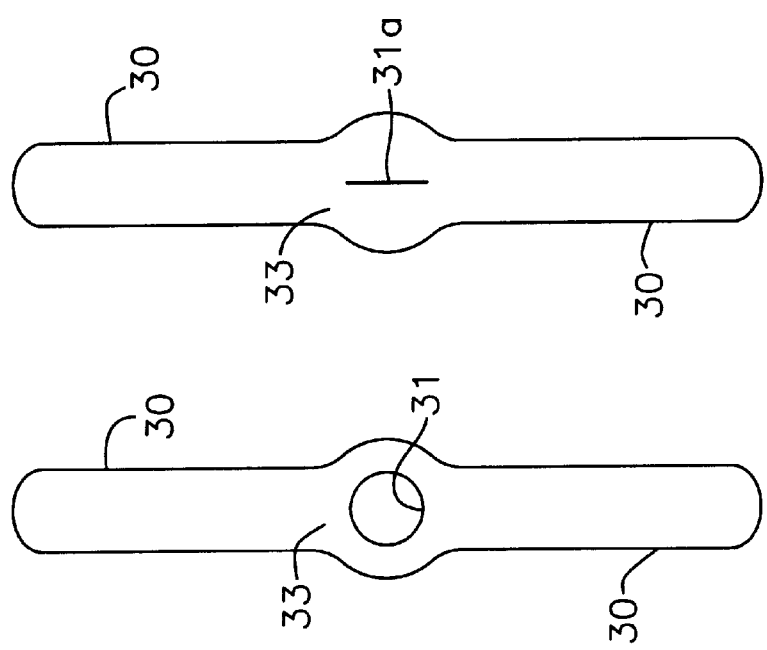
Fig. 5A  Fig. 5B  Fig. 6

PROSTHETIC LINER HAVING LONGITUDINAL INELASTICITY

BACKGROUND OF THE INVENTION

1. Field of the Invention

This invention relates, generally, to the art of prosthetics. More particularly, it relates to a cushioned prosthetic liner that expands radially but not axially.

2. Description of the Prior Art

A residual limb, or residuum, expands and contracts throughout the day and over longer periods of time as well. Accordingly, a prosthetic liner should exhibit the quality of radial expandability to accommodate such changes in size.

Prosthetic liners are worn on residual limbs to cushion the contact area between the residual limb and a prosthetic socket. Most materials having utility as cushioning means are expandable in all directions. Thus, they expand radially to accommodate during-the-day changes, as well as long-term changes, in the volume of the residual limb. Such expandability is desirable, but these liners also expand axially (longitudinally) as the patient walks. Such axial expansion is undesirable because it causes "milking" of the residual limb. The adverse effects of milking are well-known to prosthetists.

U.S. Pat. No. 4,923,474 to Klasson et al., which is incorporated hereinto by reference, relates to a cushioned prosthetic liner having a generally tubular construction and a rounded, closed distal end. In a first embodiment, Klasson et al. disclose the idea of a prosthetic liner made of a material that exhibits radial elasticity and limited longitudinal elasticity. In a second embodiment, the distal end of a prosthetic liner is if formed of an embedment material that is freely expandable in a radial and a longitudinal direction. The disclosure of the second embodiment includes a suggestion that a wire is added to the embedment material to reduce stretching in the longitudinal direction. How slipping of the wire relative to the embedment material could be prevented is untaught.

In a commercial embodiment of the Klasson et al. prosthetic liner, a fabric is laminated onto a silicone prosthetic liner to achieve the claimed properties. The fabric is of the woven, open mesh type and adequately performs its intended function. However, the fabric has the same shape as the liner, i.e., it is essentially tubular with a closed end. The fabric is laminated into the distal end of the liner, and extends roughly one-third to one-half of the longitudinal extent of the liner. The radial expandability is limited by the fact that the material completely encircles or covers the distal end of the prosthetic liner. Such a structure inherently includes substantial resistance to radial expansion.

If the wire of the second embodiment, discussed above, includes multiple wires that encircle the longitudinal axis of the prosthetic liner, those wires would present substantial resistance to radial expansion. If a single wire is used, its inherent rigidity would also present substantial resistance to radial expansion.

Significantly, the fabric stretches in the longitudinal direction and milking of the residuum results. If a wire material that somehow did not slip relative to the embedment material were substituted for the fabric, the longitudinal stretching would be overcome, but the quality of radial expandability would be diminished as aforesaid.

Prosthetic liners are typically about fourteen or so inches in length. In most cases, a few inches are trimmed from the open proximal end to accommodate bending of the patient's knee. The Klasson et al. material that provides radial expandability while inhibiting longitudinal stretching is restricted to the distal third or distal half of the liner. If it were to extend further toward the proximal, open end of the liner, it would not stretch in the anterior region when the knee is bent. There would be insufficient expandability when the knee is flexed because the embedment material would completely surround the knee.

To better appreciate why the Klasson et al. device remains subject to at least some milking action, it should be understood that the restriction of the material that permits radial expandability while resisting longitudinal stretching to the distal one-half or one-third of the liner and the elasticity of the embedment material reduces the amount of surface area over which the weight of the prosthesis may be suspended. For example, the weight of a ten pound prosthesis suspended at the end of the Klasson et al. device is spread over the two square inch area of the distal attachment plate and not over the entire inner surface of the prosthetic liner, resulting in a negative pressure of five pounds per square inch during the swing phase of the wearer's gait. This results in the milking process.

An improved cushioned prosthetic liner is needed that would spread the weight over a greater surface area to reduce the milking action.

U.S. Pat. No. 5,830,237 to Kania, which is incorporated hereinto by reference, discloses a cushioned prosthetic liner formed of a fabric where one side thereof is coated with a gel. However, the fabric is stretchable in all directions, including radial and longitudinal. Thus, the Kania structure does not perform the anti-milking function for which the Klasson et al. structure is designed.

Accordingly, there remains a need for a cushioned prosthetic liner that is expandable in a radial direction yet substantially nonexpandable in a longitudinal direction. The needed prosthetic liner should not include inherent limitations to radial expandability.

More particularly, there is a need for a prosthetic liner that exhibits substantially the same ideal properties as proposed in the Klasson et al. disclosure, but which does not include a wire or a fabric liner that only covers the lower third or lower half of the liner.

There remains a need as well for a structure that limits milking to a substantially greater degree. The improved means for preventing longitudinal stretching and allowing radial expansion should extend the entire length or substantially the entire length of the prosthetic liner without adversely affecting flexing of the knee. The improved means should include materials that are easily cuttable with ordinary scissors so that the prosthetic liner could be cut to size as needed. The materials used should not present an abrading edge when cut.

Moreover, there is a need for a cushioned prosthetic liner that spreads the suspended weight of the prosthesis over a larger surface area to reduce the effects of milking.

However, it was not obvious to those of ordinary skill in this art how the needed improvements could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. The present invention includes a prosthetic liner of generally tubular shape having a rounded, closed distal end and an open proximal end for receiving a residuum. It includes a distal attachment plate secured to the prosthetic liner at a distal end thereof and a plurality of elongate arms, having a strip or ribbon-like shape, that extend from or across the distal attachment plate in a distal-to-proximal direction. The elongate arms are equidistantly and circumferentially spaced apart with respect to one another. The distal attachment plate is formed of a substantially rigid material, and the elongate arms are flexible in a radially inward and radially outward direction with respect to a longitudinal axis of the prosthetic liner. The elongate arms are formed of a predetermined material that is substantially nonstretchable in an axial direction. Moreover, the predetermined material is nonstretchable in a transverse direction as well.

Accordingly, the elongate arms and the distal attachment plate cooperate with one another to make substantially the entire inner surface area of the prosthetic liner the surface area over which the weight of the prosthesis is spread. The surface area is sufficiently large to reduce the negative pressure generated by a prosthesis during the swing phase of a gait in pounds per square inch to a sufficiently low negative pressure to substantially prevent milking of a residual limb. In another embodiment, the elongate arms are formed integrally with the distal attachment plate, are made of the same material as the distal attachment plate, and extend to a length substantially equal to about one-half the length of the liner. When so truncated, the elongate arms are called "fingers."

Alternatively, the fingers are separately formed relative to the distal attachment plate and are made of a different material. They are mounted about a peripheral edge of the distal attachment plate in circumferentially spaced relation to one another; the fingers may extend to a length substantially equal to about one-half the length of the liner, or they may take the form of elongate arms that extend substantially the entire length of the liner.

The distal attachment plate includes a base and a neck. The base may be surface mounted on the prosthetic liner or it may be embedded therewithin. The neck protrudes outwardly from the base so that a prosthetic limb may be attached thereto.

In an additional embodiment, an elongate arm has a central aperture or slit formed therein for receiving the neck. Opposite ends of the elongate arm are then secured to an external surface of the cushioned prosthetic liner in diametrically opposed relation to one another.

There are further variations of the invention set forth below in the detailed description that follows.

It is a primary object of this invention to provide a prosthetic liner that expands radially in all directions to accommodate changes in volume of a residual limb but which is substantially inelastic in a longitudinal direction.

Another major object is to provide a prosthetic liner having a structure that effectively harnesses substantially the entire inner surface area of the liner to support the weight of a prosthesis during the swing phase of a gait so that "milking" of the residual limb is substantially eliminated.

Another object is to provide a prosthetic liner that is economical to manufacture.

Another important object is to provide an anti-milking prosthetic liner that can be cut to size to fit a residuum.

Still another object is to provide a prosthetic liner that resists longitudinal stretching and which provides radial expandability without interfering with the flexing of a knee by the user of the prosthetic liner.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a longitudinal sectional view of a first embodiment of the novel means for preventing longitudinal stretching of a prosthetic liner;

FIG. 2 is a longitudinal sectional view of a second embodiment thereof;

FIG. 3 is a longitudinal sectional view of a third embodiment thereof;

FIG. 3A is a perspective view of the distal attachment plate used in conjunction with the embodiment of FIG. 3;

FIG. 4 is a longitudinal sectional view of a fourth embodiment thereof;

FIG. 5 is a is a longitudinal sectional view of a fifth embodiment thereof;

FIG. 5A is a side elevational view of a first nonstretchable means of the type having utility in connection with the embodiment of FIG. 5;

FIG. 5B is a side elevational view of a second nonstretchable means of the type having utility in connection with the embodiment of FIG. 5;

FIG. 6 is a perspective view of a sixth embodiment thereof;

DETAILED DESCRIPTION OF THE PREFERRED EMBODIMENT

Figure 7:
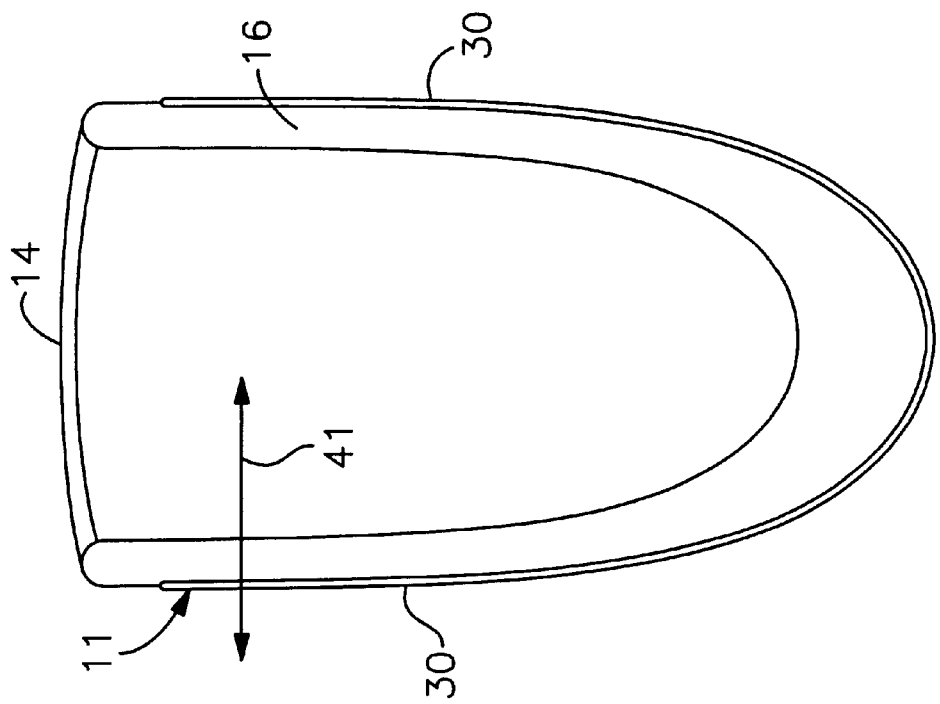
FIG. 7 is a longitudinal sectional view of a seventh embodiment thereof.

Referring now to FIG. 1, it will there be seen that an exemplary embodiment of the invention is denoted as a whole by the reference numeral 10.

Novel structure 10 includes a cushioned prosthetic liner 11 having a generally tubular shape with a rounded, closed distal end 12 and an open proximal end 14 for receiving a residuum. Note that distal end 12 is thicker, preferably, than side walls 16.

Prosthetic liner 11 is preferably formed of silicone, urethane, a thermoformable gel, or other suitable cushioning material which may be of the thermoplastic or thermosetting type.

Advantageously, various therapeutic compositions such as vitamin E, aloe vera, bactericides, and the like, may be charged into the mixture in various concentrations when the cushioning material is being prepared. The therapeutic compositions will seep out of the cushioning material over time, thereby being topically applied to the skin of the user of the prosthetic liner.

In all embodiments of the invention, a distal attachment plate 13, preferably of metallic construction, is employed to enable interconnection of a prosthetic socket, not shown, within which prosthetic liner 11 is positioned, to a prosthetic device such as an artificial leg and foot, not shown.

Each distal attachment plate has a base that is embedded in distal end 12 and a neck that protrudes from the base and extends out of the distal end. The neck includes a coupling means that releasably engages a coupler at the distal end of a prosthetic socket, not shown. Distal attachment plate 13 may also be surface mounted, i.e., the inventive structures depicted herein have utility in connection with both embedded and surface-mounted distal attachment plates.

In the embodiment of FIG. 1, base 18a is flat and neck 19a protrudes from the center thereof in coincidence with a longitudinal axis of liner 11.

In the embodiment of FIG. 2, base 18b is convex on its distal side and concave on its proximal side. Neck 19b protrudes from the center thereof.

In the embodiment of FIGS. 3 and 3A, base 18c is convex on its distal side, concave on its proximal side, and neck 19c protrudes outwardly from the center of the convex side. Significantly, base 18c includes a plurality of integrally formed elongate arms 20 that extend in a longitudinal direction therefrom, embedded within side walls 16 of prosthetic liner 11. Although two elongate arms are depicted (see FIG. 3A), spaced diametrically opposite from one another, base 18c could be constructed to have three longitudinally extending arms 20 spaced one hundred twenty degrees from one another, four arms spaced ninety degrees from one another, and so on. Base 18c could be metallic, formed of high impact plastic, and the like.

FIG. 4 depicts an embodiment that has the same base 18c as in the embodiment of FIG. 3. This embodiment adds elongate arms 30 disposed in overlying relation to the base. The arms need not be formed of a single material; for example, elongate arms 30 could include a strip of fiberglass cloth underlying or overlying a strip of silk, or the strip of material could be a composite material.

The embodiment of FIG. 5 is depicted as having the distal attachment plate of the FIG. 1 embodiment, but it should be understood that the FIG. 5 embodiment is used with the distal attachment plates of FIGS. 2 and 3 as well.

In the embodiment of FIG. 1, the respective leading ends of a plurality of nonstretchable longitudinally extending, strip-shaped elongate arms 30 are integrally formed with or attached by suitable means to base 18a at its periphery and extend therefrom in a distal-to-proximal direction. The distal ends of arms 30 overlie the distal flat face of base 18a and are preferably not connected to the extreme edge thereof. Elongate arms 30 are preferably equidistantly and circumferentially spaced apart from one another, are radially disposed with respect to a longitudinal axis of liner 11 and are equidistantly spaced from said axis when the prosthetic liner is in repose.

Significantly, elongate arms 30 are not confined to the distal end of prosthetic liner 11; they may extend to open proximal end 14 thereof. They are formed of an inelastic material such as a strip of fiberglass cloth or silk. Silk is preferred because it does not produce a rough edge when cut. It is highly inelastic when in strip form as depicted and when pulled upon in a longitudinal or transverse direction. Accordingly, it is highly effective against the "milking" phenomenon.

Significantly, elongate arms 30, collectively with distal attachment plate 13, have the effect of spreading the weight of a prosthesis attached to neck 19a throughout substantially the entire inner surface area of liner 11.

Other suitable materials for forming elongate arms 30 include carbon fiber, Kevlar®, Nylon®, Rayon®, Dacron®, thermoplastics, cotton and metal or plastic open mesh screen material. Other nonelastic materials are also within the scope of this invention; it is impractical to list all nonelastic materials.

The embodiment of FIG. 2 is the same as that of FIG. 1, differing only in that distal attachment plate 13 includes convex base 18b. In all embodiments, distal attachment plate may be made of Nylon®, metal, plastic, urethane, and combinations thereof.

There are no elongate arms 30 in the embodiment of FIG. 3. Instead, base 18c has elongate fingers, collectively denoted 20 as mentioned above, that are integrally formed with said base 18c. As best understood in connection with FIG. 3C, fingers 20 in this embodiment are two in number and are equidistantly spaced apart from one another, i.e., they are diametrically opposed to one another. The number of fingers 20 could be increased and the benefits of this invention would still be realized.

Base 18c may be formed of a metallic material, a high impact plastic, fiberglass, etc. Fingers 20 thereof are not trimmable by ordinary scissors if said fingers are integrally formed therewith. Accordingly, fingers 20 are confined to the distal region of liner 11 and do not extend to the open proximal end thereof. When such longitudinal extension is limited, the weight of a prosthesis cannot be spread out over substantially the entire inner surface area of the liner, but it is still spread out over the distal end thereof and represents a significant improvement over the structures of the prior art which concentrate the support function on the distal attachment plate alone.

It should be understood that fingers 20 need not be integrally formed with distal attachment plate 13 and thus may be formed of other materials such as strips of silk, fiberglass cloth, and the like. Accordingly, it should be understood that elongate arms 30 depicted in the embodiments of FIGS. 1 and 2, e.g., could be truncated, thereby producing fingers 20 that are not integrally formed with distal attachment plate 13 and which are formed of a material or materials that differ from that of said distal attachment plate.

In the embodiment of FIG. 4, elongate arms 30 effectively extend the length of fingers 20 all the way to open proximal end 14 or as close thereto as desired. Since elongate arms 30 are made of a nonstretchable material or materials that are easily cuttable by ordinary scissors, they may extend all the way or substantially all the way to said proximal end 14 and will not interfere with trimming of prosthetic liner 11. Accordingly, the weight of a prosthesis attached to distal attachment plate 13 is spread substantially throughout the inner surface area of liner 11 and milking is reduced to a minimum.

In FIGS. 1–4, elongate arms 30 are embedded within the cushioning material that forms prosthetic liner 11. In FIG. 5, elongate arms 30 are positioned on the external surface of said liner.

As best understood in connection with FIGS. 5, 5A, and 5B, an elongate arm 30 is centrally apertured as at 31 or centrally slit as at 31a and is preferably bulged somewhat at its midregion 33. The bulge provides structural reinforcement and helps to further spread the weight of a prosthesis but is not critical. Neck 19a is received within central opening such as aperture 31 or slit 31a when elongate arm 30 is placed into overlying relation to prosthetic liner 11, as depicted in FIG. 5. A second strip of the same construction could be added, at a ninety degree angle to the first, to provide four elongate arms 30 that are spaced ninety degrees from one another.

Alternatively, the same effect is achieved by providing strips having a length about half that of the strips depicted in FIGS. 5A and 5B, and forming an aperture or slit adjacent an end thereof. Plural amounts of said strips are then attached at their respective apertures to neck 19a and arranged in a radial pattern relative to said neck so that said strips are equidistantly and circumferentially spaced about the surface of the liner so as to perform the same function as the centrally apertured strips.

In all of the embodiments that include elongate arms 30, the longitudinal nonstretchability of said elongate arms prevents longitudinal stretching of liner 11 and thus inhibits the "milking" phenomenon to a greater extent than any liner heretofore known. Moreover, said elongate arms spread the weight of a suspended prosthesis throughout the inner surface area of the liner until the negative pressure per square inch is very small. In the embodiment of FIG. 3, truncate fingers 20 perform the same function, to a lesser degree.

Elongate arms 30 can be made of any non-stretchable material, but materials that are easy to cut with conventional scissors and that do not have rough edges when cut are preferred so that they can extend to open proximal end 14 and thus spread the prosthesis weight over the inner surface area of the prosthetic liner.

For example, an elongate strip of silk is substantially non-stretchable in the longitudinal direction and is easy to cut with conventional scissors. Thus, when silk arms 30 are used, they may extend all the way or substantially all the way to the proximal open end of the liner, and the liner may be cut to size by the patient or the prosthetist without regard to the silk. Not only is the silk easy to cut with conventional scissors, it also does not present a rough edge where cut. It is more desirable than fiberglass cloth and numerous other nonstretchable materials in this respect.

In the embodiment of FIG. 6, plural strips 40 of epoxy are applied to the external surface of prosthetic liner 11. As is the case with truncate fingers 20 and elongate arms 30, strips 40 may be two in number and diametrically opposed to one another, three in number and disposed at one hundred twenty degree intervals about the periphery of prosthetic liner 11, and so on. Once dry, these strips are nonstretchable. In this way, a prosthetic liner of the type heretofore known may be treated with elongate narrow strips of epoxy or other suitable adhesive that is nonstretchable after curing, and thereby converted into a non-milking liner.

FIG. 6 may also be construed as depicting strips 40 that are not made of epoxy, but rather of a nonstretchable material, such as silk, that are sewed onto a prosthetic liner of the prior art. In this way, a conventional prosthetic liner may be retrofit with strips 40 to prevent the milking phenomenon.

FIG. 6 may also be interpreted as depicting neither epoxy nor any other nonstretchable material. Instead, the longitudinal edges of strips 40 may be interpreted as depicting seam lines created by sewing a nonstretchable thread along the extent of the prosthetic liner. Whether the seams are straight, or curved as in the Kania liner, such nonstretchable seams will provide the needed resistance to longitudinal stretching.

Figure 8:
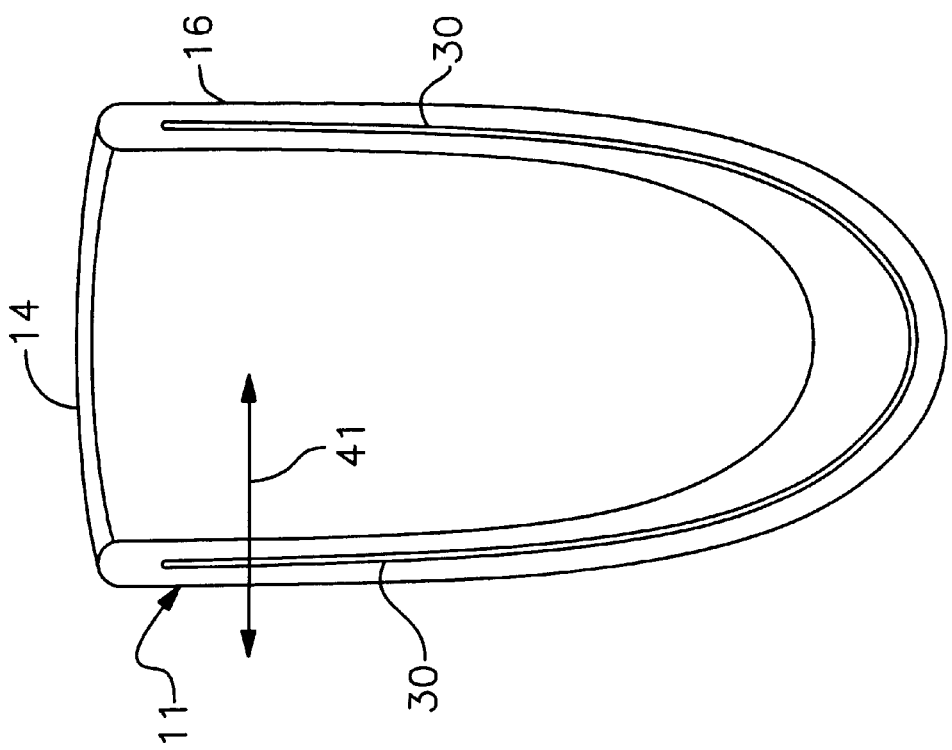
FIG. 8 is a longitudinal sectional view of an eighth embodiment thereof.

FIGS. 7 and 8 depict a prosthetic liner 11 having no distal attachment plate. In the embodiment of FIG. 7, elongate arms 30 are embedded in the liner as depicted and perform the same function as in the earlier embodiments.

In the embodiment of FIG. 8, elongate arms 30 are provided in the form of plural elongate strips of nonstretchable material 31 that are laminated into or otherwise secured to the external surface of liner 11 by any suitable means. In a preferred method for making a liner as depicted in FIG. 8, plural strips of silk, fiberglass cloth, or the like are placed into overlying relation to a tubular cushioned prosthetic liner. Two strips may be disposed in diametrically opposed relation to one another, three strips may be disposed in one hundred twenty degree spaced apart relation to one another, and so on. No strip is placed in the anterior region where it could interfere with knee flexing. A thin layer of silicone is then applied over the strip of nonstretchable material to bond it to the surface of the liner, and a thin Nylon® cover is then applied in a well-known way to reduce the friction generated by inserting the liner into a prosthetic socket.

As in the other embodiments of this invention, each strip of nonstretchable material may be provided in the form of two or more strips of nonstretchable material disposed in vertically stacked relation to one another, as mentioned above. For example, each strip 20, 30, or 31 may be provided in the form of a strip of silk disposed in overlying relation to a strip of fiberglass cloth.

As indicated by double-headed directional arrows 41 in FIGS. 1–8, prosthetic liner 11 is easily flexed in a radially inward or radially outward direction, relative to a longitudinal axis of liner 11. This is because truncate fingers 20, or elongate arms 30, or strips of nonstretchable material 31, or strips of epoxy 40, or seams created by sewing are relatively narrow, longitudinally disposed, circumferentially spaced apart members that offer little or no resistance to radial movement. Thus, when embedded in a prosthetic liner formed of silicone or other suitable cushioning material, or positioned on the surface thereof, the inherent bias of the prosthetic liner allows it to conform to the residual limb as it expands and contracts, without substantial resistance offered by said fingers, arms, strips, or seams. This is in sharp and distinctive contrast to the prosthetic liner of Klasson et al. where a fabric material covers the surface of the distal end of the prosthetic liner, thereby limiting such radial expansion and contraction.

Since the fingers, arms, epoxy strips, nonstretchable material strips, or seams of this inventive structure are made of fiberglass cloth, silk, epoxy or other nonstretchable material, said fingers, arms, strips or seams are not extensible or contractible in an axial direction. Thus, they prevent milking of the residuum while allowing it to radially expand and contract.

The distal attachment plate may be embedded within the prosthetic liner at any preselected depth from the exterior surface. Alternatively, it may be placed on the exterior surface of prosthetic liner 11 and then secured thereto by lamination of a thin, additional layer of adhesive or other suitable cushioning material.

Significantly, the novel elongate arms, strips or seams create a structure that has the effect of substantially increasing the inner surface area of the prosthetic liner over which a prosthesis is suspended. Substantially the entire inner surface area of the prosthetic liner is harnessed. In a commercial embodiment of the novel cushioned prosthetic liner, the weight of a ten pound prosthesis is spread out over a one hundred sixty eight square inch area. Thus, when the prosthesis is suspended during the swing phase of the gait, the negative pressure is only six hundredths of a pound per square inch (0.06 lbs/in$^2$). This represents a revolutionary improvement over the negative five pounds per square inch stresses that appear in earlier prosthetic liners.

Since the elongate arms, strips, or seams do not completely surround the prosthetic liner, they do not inhibit flexing of the prosthetic liner in the anterior region and thus the knee of a wearer is freely bendable.

This invention represents a major breakthrough in the art of prosthetic liners. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, What is claimed is:

1. A prosthetic apparatus, comprising:
   a prosthetic liner of generally tubular shape having a rounded, closed distal end and an open proximal end for receiving a residuum;
   a distal attachment plate secured to said prosthetic liner at said distal end thereof;
   a plurality of elongate arms extending from said distal attachment plate in a distal-to-proximal direction;
   said elongate arms being circumferentially spaced apart with respect to one another;
   said elongate arms being flexible in a radially inward and radially outward direction with respect to a longitudinal axis of said prosthetic liner; and
   said elongate arms being formed of a predetermined material that is substantially nonstretchable in an axial direction;
   whereby said elongate arms and said distal attachment plate cooperate with one another to spread the weight of a prosthesis attached to said distal attachment plate to thereby reduce a negative pressure in pounds per square inch exerted by said prosthesis during the swing phase of a gait.

2. The prosthetic apparatus of claim 1, wherein said elongate arms are formed integrally with said distal attachment plate and extend to a length substantially equal to about one-half the length of the prosthetic liner.

3. The prosthetic apparatus of claim 1, wherein said elongate arms are separately formed relative to said distal attachment plate and extend to a length substantially equal to about one-half the length of the prosthetic liner.

4. The prosthetic apparatus of claim 1, wherein said elongate arms are separately formed relative to said distal attachment plate and are mounted about a peripheral edge of said distal attachment plate in circumferentially spaced relation to one another and wherein said elongate arms extend substantially the entire length of said prosthetic liner.

5. The prosthetic apparatus of claim 1, wherein said distal attachment plate includes a base and a neck, said base being secured to said prosthetic liner and said neck protruding outwardly therefrom, and wherein an elongate arm has a central opening formed therein, said central opening receiving said neck and opposite ends of said elongate arm being secured to an external surface of said prosthetic liner.

6. The prosthetic apparatus of claim 1, wherein said predetermined material is silk so that it is easily cuttable and so that no abrading edge is created when it is cut, whereby the prosthetic liner may be cut to size as desired to fit a residuum.

7. The prosthetic apparatus of claim 1, wherein the predetermined material is fiberglass cloth.

8. The prosthetic apparatus of claim 1, wherein the predetermined material is a carbon fiber.

9. The prosthetic apparatus of claim 1, wherein the predetermined material is a synthetic material.

10. The prosthetic apparatus of claim 1, wherein the predetermined material is a metallic open mesh screen material.

11. The prosthetic apparatus of claim 1, wherein the predetermined material is a plastic open mesh screen material.

12. The prosthetic apparatus of claim 1, wherein said elongate arms are formed of differing predetermined materials where one of said predetermined materials underlies the other of said predetermined materials.

13. The prosthetic apparatus of claim 1, wherein the predetermined material is an epoxy that is nonstretchable after curing, said epoxy disposed in equidistantly and circumferentially spaced apart elongate strips to an external surface of said prosthetic liner.

14. The prosthetic apparatus of claim 13, wherein said strips of epoxy are disposed on a prosthetic liner formed of a material that is stretchable in a radial and longitudinal direction so that said epoxy, when cured, prevents stretching of said material in a longitudinal direction and allows stretching of said material in a radial direction.

15. The prosthetic apparatus of claim 1, wherein said elongate arms are provided in the form of seams formed by sewing, said seams extending substantially the entire longitudinal extent of said prosthetic liner.

16. A prosthetic liner of generally tubular shape having a rounded, closed distal end and an open proximal end for receiving a residuum, comprising:
   said prosthetic liner formed of a cushioning material selected from the group consisting of silicone, urethane, and thermoformable gels;
   a plurality of elongate arms extending continuously from said closed distal end in a distal-to-proximal direction;
   said elongate arms being circumferentially spaced apart with respect to one another;
   said elongate arms being flexible in a radially inward and radially outward direction with respect to a longitudinal axis of said prosthetic liner;
   said elongate arms being formed of a predetermined material that is substantially nonstretchable in an axial direction; and
   said elongate arms being embedded within said prosthetic liner.

17. A prosthetic liner of generally tubular shape having a rounded, closed distal end and an open proximal end for receiving a residuum, comprising:
   said prosthetic liner formed of a cushioning material selected from the group consisting of silicone, urethane, and thermoformable gels;
   a plurality of elongate arms extending continuously from said closed distal end in a distal-to-proximal direction;
   said elongate arms being circumferentially spaced apart with respect to one another;
   said elongate arms being flexible in a radially inward and radially outward direction with respect to a longitudinal axis of said prosthetic liner;
   said elongate arms being formed of a predetermined material that is substantially nonstretchable in an axial direction; and
   said elongate arms being secured to an exterior surface of said prosthetic liner.

* * * * *

EX PARTE REEXAMINATION CERTIFICATE (7931st)
United States Patent
Fay

(10) Number: US 6,231,617 C1
(45) Certificate Issued: Dec. 14, 2010

(54) PROSTHETIC LINER HAVING LONGITUDINAL INELASTICITY

(75) Inventor: John N. Fay, St. Petersburg, FL (US)

(73) Assignee: Thermo-Ply, Inc., St. Petersburg, FL (US)

Reexamination Request:
No. 90/010,917, Apr. 1, 2010

Reexamination Certificate for:
Patent No.: 6,231,617
Issued: May 15, 2001
Appl. No.: 09/352,107
Filed: Jul. 14, 1999

(51) Int. Cl.
*A61F 2/78* (2006.01)
*A61F 2/50* (2006.01)
*A61F 2/80* (2006.01)

(52) U.S. Cl. .......................................... 623/36
(58) Field of Classification Search ................. None
See application file for complete search history.

(56) References Cited

U.S. PATENT DOCUMENTS

| 3,084,685 A | 4/1963 | Lewis |
| 4,923,474 A | 5/1990 | Klasson et al. |
| 5,957,980 A | 9/1999 | Houser |
| 6,136,039 A | 10/2000 | Kristinsson et al. |

FOREIGN PATENT DOCUMENTS

WO  WO 98/04218  2/1998

*Primary Examiner*—David O. Reip

(57) ABSTRACT

A cushioned prosthetic liner includes a distal attachment plate to which is secured a number of longitudinally extending elongate arms that are substantially non-stretchable in a longitudinal direction. The arms allow radial expansion and contraction of the liner but substantially inhibit axial stretching and therefore inhibit milking of a residuum. The arms may be embedded within the liner or secured to a surface of the liner. The structure spreads the negative pressure generated during the swing phase of a gait over substantially all of the inner surface area of the liner to further inhibit the milking effect. The elongate arms are preferably formed of silk, fiberglass cloth, or other substantially non-stretchable material. They may also be provided in the form of a strip of epoxy applied to a surface of a conventional prosthetic liner or in the form of seams sewed into the liner. Additional embodiments include prosthetic liners having no distal attachment plate. In those additional embodiments, the non-stretchable elongate arms are embedded into or secured to the surface of the prosthetic liner.

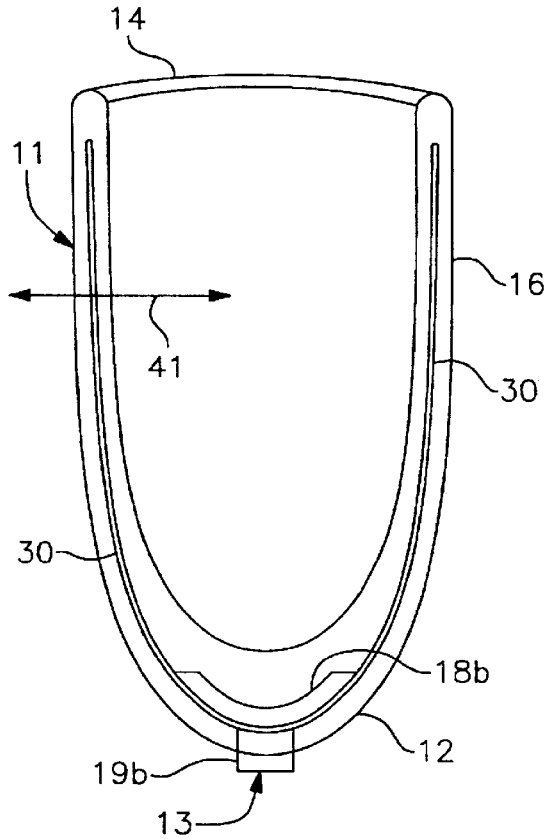

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1, 3, 5, 9, 10 and 15-17 is confirmed.

Claims 2, 4, 6-8 and 11-14 were not reexamined.

* * * * *